United States Patent [19]

Rowley et al.

[11] 4,220,722

[45] Sep. 2, 1980

[54] METHOD FOR CONJUGATING TO POLYAMINO COMPOUNDS EMPLOYING HALOACYL GROUPS AND COMPOSITIONS PREPARED THEREBY

[75] Inventors: Gerald L. Rowley, San Jose; Danton Leung, Campbell; Prithiphal Singh, Santa Clara, all of Calif.

[73] Assignee: Syva Company, Palo Alto, Calif.

[21] Appl. No.: 876,772

[22] Filed: Feb. 10, 1978

[51] Int. Cl.² ............................................. C12N 9/96
[52] U.S. Cl. .................................... 435/188; 435/177; 435/7; 260/112 R; 424/12; 260/112 B; 260/112.5 R; 260/112.7
[58] Field of Search .................... 195/63, 68, DIG. 11; 260/112 R; 424/12; 435/7, 177, 174, 188

[56] References Cited

U.S. PATENT DOCUMENTS

| | | | |
|---|---|---|---|
| 4,067,774 | 1/1978 | Rubenstein | 195/63 |
| 4,100,268 | 7/1978 | Scherr | 424/12 |
| 4,144,131 | 3/1979 | Richardson | 195/68 |

*Primary Examiner*—Lionel M. Shapiro
*Attorney, Agent, or Firm*—Bertram I. Rowland

[57] ABSTRACT

Methods and compositions are provided for conjugating a wide variety of compounds, particularly polyfunctional compounds, having a mercapto group, either naturally present or synthetically introduced, to a polyamino compound, particularly a polypeptide (including proteins). The method employs a haloalkylcarbonyl compound, which is conjugated to one or more of the amino groups under mild acylating conditions. This is followed by combining the acylated polyamino compound with a mercapto containing compound, whereby the halogen is displaced by the sulfur of the mercapto group to form a stable thioether linkage. The resulting conjugates, depending on the compounds involved, can find uses in immunoassays, as hapten-antigen conjugates for the production of antibodies, and as ligand analog enzyme conjugates for use as reagents in controlling the distribution of substitution of a mercapto compound to a polyamino compound.

14 Claims, No Drawings

METHOD FOR CONJUGATING TO POLYAMINO COMPOUNDS EMPLOYING HALOACYL GROUPS AND COMPOSITIONS PREPARED THEREBY

BACKGROUND OF THE INVENTION

1. Field of the Invention

There is a continuously expanding interest in being able to conjugate, frequently selectively, a compound to another compound which is polyfunctional. Where both compounds are polyfunctional, the problem of conjugation is exacerbated, if one does not wish all of the functional groups to participate in the reaction. Also, the need to functionalize a polyfunctional compound for conjugating to a polyamino compound will frequently require the introduction of protective groups for alcohols and amines, so that the reactive functionality does not polymerize the compound to be conjugated.

One area of particular interest is the conjugation of a wide variety of haptens and antigens to polypeptides (including proteins), particularly where conjugation is to occur at available amino groups. In preparing antibodies for use in competitive protein binding assays, where the analyte of interest is haptenic, it is generally necessary to conjugate the hapten to an antigen, normally a protein. Where the analyte has a plurality of functionalities which can react with the active functionality to be used for conjugating to the polypeptide, it becomes necessary to introduce removable protective groups to prevent polymerization of the analyte. After conjugation, it is usually difficult to efficiently remove the protective groups.

Where the conjugate is to be used for the preparation of antibodies, the resulting antibodies not only recognize the analyte of interest, but the analyte having the protective groups. This may result in substantially reducing the specificity of the antibody composition for the analyte of interest.

One class of competitive protein binding assays involves the use of enzymes as a label. It is necessary to conjugate the analyte of interest to the enzyme. It is desirable that certain reactive site positions on the enzyme be preferentially conjugated as compared to other reactive site positions. A method which would provide the ability to discriminate to even a partial degree is desirable.

In addition, to have an enzyme which has been modified, whereby the same sites will be conjugated to analytes, regardless of the particular analyte, can provide a number of advantages. For example, in one of the assays which employs an enzyme as a label, it is desirable that the enzyme retain a substantial proportion of its initial activity after conjugation, but when antibody or other receptor is bound to the analytes conjugated to the enzyme, the enzymatic activity is substantially reduced. The fewer the analytes necessary to conjugate to the antibody to obtain the desired degree of reduction is enzymatic activity upon the binding of antibody or other receptor to the conjugated analyte, the more sensitive will be the assay response.

In addition, where a universal reagent can be employed for conjugation, greatly increased experience can be obtained in the handling of the compounds, the reacting of the compounds, as well as the subsequent handling and treatment after conjugation. This can provide for great efficiencies in synthesizing and subsequent formulation.

DESCRIPTION OF THE PRIOR ART

Kato, et al, Eur. J. Biochem. 62, 285 (1976), discloses the use of maleic anhydride with a polyamino compound to provide one or more maleimide groups, followed by the addition of a compound with a mercapto group to add to the double bond of the maleimide. See also, Lee and Kenny, Clinical Chem. 21,967(1975).

SUMMARY OF THE INVENTION

Methods and compositions are provided for combining a polyfunctional compound having a plurality of reactive primary and/or secondary amino functionalities with a second compound having a mercapto functionality, usually polyfunctional, having functionalities reactive to acyl groups e.g. hydroxylic and amino. The polyamino compound is initially reacted with a linking compound having an active halogen or pseudohalogen and a non-oxo carbonyl functionality for reacting with at least one of the amino functionalities. The mercapto compound is then added to the halo or pseudohalo containing polyamino compound for substitution of the halo groups to provide a thioether linked conjugate of the mercapto compound with the polyamino compound.

The method finds particular use in the preparation of polypeptide and protein conjugates for preparing antigens, enzyme conjugates for immunoassays, fluorescent labeling of polypeptides and proteins and the like. By employing the subject method, one can obtain a consistent pattern of substitution, the conjugation can be carried out under extremely mild conditions and some control of the positions of substitution can be achieved.

DESCRIPTION OF THE SPECIFIC EMBODIMENTS

The method of the subject invention involves the labeling as a first step of a poly(amino acid) compound, normally a polypeptide or protein, with a compound having an $\alpha$-halo or $\alpha$-pseudohaloalkylcarbonyl functionality and a non-oxo carbonyl functionality (including the nitrogen analog, imido, and sulfur analog, thiono), which may be the same or different from the carbonyl of the $\alpha$-halo or $\alpha$-pseudohaloalkylcarbonyl functionality. The reaction is carried out in a normally aqueous medium under mild pH conditions, generally at 9.5 or below, so as to form an amide (including the nitrogen and sulfur analogs, imidine and thioamide respectively). The product may then be purified under conventional conditions and the halo or pseudohalo substituted by a mercaptan under mild conditions in an aqueous solution at moderate pH, normally basic pH. The product may then be worked up and isolated.

The compounds prepared in accordance with this invention have many uses, for example haptens or antigens may be conjugated to labels, such as fluorescers and enzymes, and the resulting compounds employed in immunoassays for the determination of such haptens and antigens. In addition, haptens may be conjugated to antigens to be used for the production of antibodies, which may also serve as reagents in immunoassays.

The subject method provides a means for preparing derivatives of polyamino compounds, which have a limited number of active sites. The distribution of these active sites may be retained substantially constant, so that when conjugating haptens and antigens to the polyamino compounds, substitution will be relatively uniform, regardless of the particular compound which is conjugated.

In addition, it will normally be found that due to the position of the halo substituent on the polyamino compound, the halo compounds may have varying activities. One can then distinguish between the varying activities, by employing two different mercaptan reagents, the first reagent being added in a sufficient amount to react with all or substantially all of the more reactive halogen. In this manner, the mercaptan compound of interest may be directed either to the more or less reactive sites. Also, the subject method provides for synthetic convenience, for so far as the polyamino compound, the same compound may be repetitively prepared, regardless of the compound to which it is to be conjugated.

MATERIALS

The materials which are employed in the subject invention are the active halogen or pseudohalogen compound, the polyamino polyfunctional compound to which the halo or pseudohalo compound is conjugated, and the mercaptan which is employed for substitution on the halogen or pseudohalogen.

The first compounds to be considered will be the halo or pseudohalo compounds. These compounds will normally be of from 2 to 20, more usually of from 2 to 16 carbon atoms, and preferably of from about 2 to 12 carbon atoms. Other than the halo or pseudohalo group, the compound will normally have at least two heteroatoms, and may have as many as 20 heteroatoms, more usually having from about 2 to 12 heteroatoms, and preferably from about 2 to 8 heteroatoms. The heteroatoms will normally be oxygen, nitrogen and sulfur or any appropriate counterion for a charged species. Oxygen will normally be present as in nitro, oxo or ether (an ester includes oxo and ether oxygens); nitrogen will be present as in nitro, amido, or bonded solely to carbon, e.g. tertiary amine; and sulfur will be present as thiono or thioether. The compounds will of necessity include aliphatic groups, but may also include alicyclic, aromatic, and heterocyclic groups.

For the most part, the compounds used for conjugation to the amino functionalized compounds will have the following formula:

wherein:
X—Cl,Br,CH$_3$SO$_3$ (mesylate), preferably Br;
Y and Y$^1$—O, NH, S, preferably O;
A—NH, O, preferably NH;
D—chain of from 1 to 9, usually 1 to 6 atoms in the chain, having a total number of atoms other than hydrogen of from 1 to 12, usually 1 to 10, preferably 1 to 6, which may be C, O, N and S, usually C, O and N, wherein: O is present as oxo or ether, particularly non-oxo carbonyl; N is present as amido or bonded solely to carbon and may be present as terminal nitrogen doubly bonded to (CY$^1$) where Y$^1$ is S to form isothiocyanate; and S is present as thiono or thioether; preferably hydrocarbon to form a hydrocarbylene group which may be aliphatic, alicyclic, aromatic or combinations thereof, preferably aliphatic, which may be aliphatically saturated or unsaturated having from 0 to 1 site of unsaturation i.e. ethylenic and acetylenic, preferably saturated and may be straight or branched chain, preferably straight chain;

Z—OV or OCO-alkyl, wherein alkyl is of from 1 to 6, usually 1 to 4 carbon atoms and V is hydrogen, p-nitrophenyl, N-oxy succinimide, or when Y is NH and m is zero, or Y$^1$ is NH and m is 1, alkyl of from 1 to 6 carbon atoms.

k, m and p—zero or 1, wherein p is zero when D and (CY$^1$) form an isothiocyanate group The preferred halo compounds of this invention will have the following formula:

wherein:
Y$^2$ and Y$^3$—O, NH, preferably O
D$^1$—alkylene of from 1 to 8, usually 1 to 4 carbon atoms
Z$^1$—the same as Z, usually OH or N-oxy succinimide Illustrative compounds include N-bromoacetyl glycine, N-bromoacetyl valine, N-bromoacetyl 4-aminobutyric acid, N-bromoacetyl 3-aminopropionic acid, p-chloroacetylbenzoic acid, p-bromoacetylphenylacetic acid, N-bromoacetyl 4-aminocrotonic acid, their p-nitrophenyl esters, their N-succinimidyl esters, p-chloroacetylphenyl isothiocyanate, and methyl N-bromoacetyl glycinimidate.

The next group of compounds to be considered, are the polyamino functionalized compounds, which are primarily polypeptides and proteins, but may also include polyglucosamines and nucleic acids. These compounds may be included in combinations or assemblages which include bacteria, viruses, chromosomes, genes, mitochondria, nuclei, cell membranes and the like.

For the most part, the compounds will have a molecular weight of at least about 5,000, more usually at least about 10,000. In the poly(amino acid) category (includes polypeptides and proteins), the poly(amino acids) of interest will generally be from about 5,000 to 5,000,000 molecular weight, more usually from about 20,000 to 1,000,000 molecular weight. In this category, hormones of interest will generally range from about 5,000 to 60,000 molecular weight. Enzymes of interest will generally range from about 10,000 to 300,000 molecular weight. Immunoglobulins and portions thereof e.g. Fab fragments and Bence-Jones proteins, will generally range from about 23,000 to 1,000,000, with the immunoglobulins generally ranging from 150,000 to 1,000,000.

The wide variety of proteins may be considered as to the family of proteins having similar structural features, proteins having particular biological functions, proteins related to specific microorganisms, particularly disease causing microorganisms, etc.

The following are classes of proteins related by structure:
protamines
histones
albumins
globulins
scleroproteins
Phosphoproteins
mucoproteins
chromoproteins
lipoproteins nucleoproteins
glycoproteins
unclassified proteins, e.g. somatotropin, prolactin, insulin, pepsin A number of proteins found in the human plasma are important clinically and include:
Prealbumin
Albumin
$\alpha_1$-Lipoprotein
$\alpha_1$-Acid glycoprotein
$\alpha_1$-Antitrypsin
$\alpha_1$Glycoprotein
Transcortin
4.6S-Postalbumin
Tryptophan-poor
$\alpha_1$-glycoprotein
$\alpha_1$X-Glycoprotein
Thyroxin-binding globulin
Inter-$\alpha$-trypsin-inhibitor
Gc-globulin
(Gc 1-1)
(Gc 2-1)
(Gc 2-2)
Haptoglobin
(Hp 1-1)
(Hp 2-1)
(Hp 2-2)
Ceruloplasmin
Cholinesterase
$\alpha_2$-Lipoprotein(s)
$\alpha_2$-Macroglobulin
$\alpha_2$-HS-glycoprotein
Zn-$\alpha_2$-glycoprotein
$\alpha_2$-Neuramino-glycoprotein
Erythropoietin
$\beta$-lipoprotein
Transferrin
Hemopexin
Fibrinogen
Plasminogen
$\beta_2$-glycoprotein I
$\beta_2$-glycoprotein II
Immunoglobulin G
(IgG) or $\gamma$G-globulin
Mol. formula:
$\gamma_2\kappa_2$ or $\gamma_2\lambda_2$
Immunoglobulin A (IgA) or $\gamma$A-globulin
Mol. formula:
$(\alpha_2\kappa_2)^n$ or $(\alpha_2\lambda_2)^n$
Immunoglobulin M
(IgM) or $\gamma$M-globulin
Mol. formula:
$(\mu_2\kappa_2)^5$ or $(\mu_2\lambda_2)^5$
Immunoglobulin D(IgD) or $\gamma$D-Globulin ($\gamma$D)
Mol. formula:
$(\delta_2\kappa_2)$ or $(\delta_2\lambda_2)$
Immunoglobulin E (IgE) or $\gamma$E-Globulin ($\gamma$E)
Mol. formula:
$(\epsilon_2\kappa_2)$ or $(\epsilon_2\lambda_2)$
Free K and $\gamma$ light chains
Complement factors:
C'1
C'1q
C'1r
C'1s
C'2
C'3
$\beta_1$A
$\alpha_2$ D
C'4
C'5
C'6
C'7
C'8
C'9

Important blood clotting factors include:

| BLOOD CLOTTING FACTORS | |
| --- | --- |
| International designation | Name |
| I | Fibrinogen |
| II | Prothrombin |
| IIa | Thrombin |
| III | Tissue thromboplastin |
| V and VI | Proaccelerin, accelerator globulin |
| VII | Proconvertin |
| VIII | Antihemophilic globulin (AHG) |
| IX | Christmas factor, plasma thromboplastin component (PTC) |
| X | Stuart-Prower factor, autoprothrombin III |
| XI | Plasma thromboplastin antecedent (PTA) |
| XII | Hagemann factor |
| XIII | Fibrin-stabilizing factor |

Important protein hormones include:
Peptide and Protein Hormones
Parathyroid hormone (parathromone)
Thyrocalcitonin
Insulin
Glucagon
Relaxin
Erythropoietin
Melanotropin (melanocyte-stimulating hormone; intermedin)
Somatotropin (growth hormone)
Corticotropin (adrenocorticotropic hormone)
Thyrotropin
Follicle-stimulating hormone
Luteinizing hormone (interstitial cell-stimulating hormone)
Luteomammotropic hormone (luteotropin, prolactin)
Gonadotropin (chorionic gonadotropin)
Tissue Hormones
Secretin
Gastrin
Angiotensin I and II
Bradykinin
Human placental lactogen
Peptide Hormones from the Neurohypophysis
Oxytocin
Vasopressin
Releasing factors (RF)
CRF, LRF, TRF, Somatotropin-RF, GRF, FSH-RF, PIF, MIF The microorganisms which are assayed may be intact, lysed, ground or otherwise fragmented, and the resulting composition or portion, e.g. by extraction, assayed. Microorganisms of interest include:
Corynebacteria
Corynebacterium diptheriae
Pneumococci
Diplococcus pneumoniae
Streptococci
Streptococcus pyogenes
Streptococcus salivarus Staphylococci
Staphylococcus aureus
Staphylococcus albus
Neisseriae
Neisseria meningitidis
Neisseria gonorrheae

| Enterobacteriaciae | |
|---|---|
| *Escherichia coli* <br> *Aerobacter aerogenes* <br> *Klebsiella pneumoniae* | The coliform bacteria |
| *Salmonella typhosa* <br> *Salmonella choleraesuis* <br> *Salmonella typhimurium* | The Salmonellae |
| *Shigella dysenteriae* <br> *Shigella schmitzii* <br> *Shigella arabinotarda* <br> *Shigella flexneri* <br> *Shigella boydii* <br> *Shigella Sonnei* | The Shigellae |
| Other enteric bacilli | |
| *Proteus vulgaris* <br> *Proteus mirabilis* <br> *Proteus morgani* | Proteus species |
| *Pseudomonas aeruginosa* <br> *Alcaligenes faecalis* <br> *Vibrio cholerae* | |

Hemophilus-Bordetella group
Hemophilus influenzae,
  H. ducreyi
  H. hemophilus
  H. aegypticus
  H. paraiufluenzae
Bordetella pertussis
Pasteurellae
Pasteurella pestis
Pasteurella tulareusis
Brucellae
Brucella melitensis
Brucella abortus
Brucella suis
Aerobic Spore-forming Bacilli
Bacillus anthracis
Bacillus subtilis
Bacillus megaterium
Bacillus cereus
Anaerobic Spore-forming Bacilli
Clostridium botulinum
Clostridium tetani
Clostridium perfringens
Clostridium novyi
Clostridium septicum
Clostridium histolyticum
Clostridium tertium
Clostridium bifermentans
Clostridium sporogenes
Mycobacteria
Mycobacterium tuberculosis hominis
Mycobacterium bovis
Mycobacterium avium
Mycobacterium leprae
Mycobacterium paratuberculosis
Actinomycetes (fungus-like bacteria)
Actinomyces israelii
Actinomyces bovis
Actinomyces naeslundii
Nocardia asteroides
Nocardia brasiliensis
The Spirochetes Treponema pallidum
Treponema pertenue
Treponema carateum
Borrelia recurrentis
Leptospira icterohemorrhagiae
Leptospira canicola
Spirillum minus
Streptobacillus moniliformis
Mycoplasmas
Mycoplasma pneumoniae
Other pathogens
Listeria monocytogenes
Erysipelothrix rhusiopathiae
Streptobacillus moniliformis
Donvania granulomatis
Bartonella bacilliformis
Rickettsiae (bacteria-like parasites)
Rickettsia prowazekii
Rickettsia mooseri
Rickettsia rickettsii
Rickettsia conori
Rickettsia australis
Rickettsia sibiricus
Rickettsia akari
Rickettsia tsutsugamushi
Rickettsia burnetii
Rickettsia quintana
Chlamydia (unclassifiable parasites bacterial/viral)
Chlamydia agents (naming uncertain)
Fungi
Cryptococcus neoformans
Blastomyces dermatidis
Histoplasma capsulatum
Coccidioides immitis
Paracoccidioides brasiliensis
Candida albicans
Aspergillus fumigatus
Mucor corymbifer (Absidia corymbifera)

| *Rhizopus oryzae* <br> *Rhizopus arrhizus* <br> *Rhizopus nigricans* | Phycomycetes |
|---|---|

Sporotrichum schenkii
Fonsecaea pedrosoi
Fonsecaea compacta
Fonsecaea dermatitidis
Cladosporium carrionii
Phialophora verrucosa
Aspergillus nidulans
Madurella mycetomi
Madurella grisea
Allescheria boydii
Phialosphora jeanselmei
Microsporum gypseum
Trichophyton mentagrophytes
Keratinomyces ajelloi
Microsporum canis
Trichophyton rubrum
Microsporum andouini
Viruses
Adenoviruses
Herpes viruses
Herpes simplex
Varicella (Chicken pox)
Herpes Zoster (Shingles)
Virus B Cytomegalovirus
Pox Viruses
Variola (smallpox)
Vaccinia
Poxvirus bovis
Paravaccinia
Molluscum contagiosum
Picornaviruses
Poliovirus
Coxsackievirus
Echoviruses
Rhinoviruses
Myxoviruses
Influenza (A, B, and C)
Parainfluenza (1-4)
Mumps Virus
Newcastle Disease Virus
Measles Virus
Rinderpest Virus
Canine Distemper Virus
Respiratory Syncytial Virus
Rubella Virus
Arboviruses
Eastern Equine Eucephalitis Virus
Western Equine Eucephalitis Virus
Sindbis Virus
Chikugunya Virus
Semliki Forest Virus
Mayora Virus
St. Louis Encephalitis Virus
California Encephalitis Virus
Colorado Tick Fever Virus
Yellow Fever Virus
Dengue Virus
Reoviruses
Reovirus Types 1-3
Hepatitis
Hepatitis A Virus
Hepatitis B Virus
Tumor Viruses
Rauscher Leukemia Virus
Gross Virus
Maloney Leukemia Virus Enzymes of interest are clasified in accordance with the I.U.B. classification as follows:
1. Oxidoreductases
  1.1 Acting on the CH-OH group of donors
    1.1.1 With NAD or NADP as acceptor
      1. alcohol dehydrogenase
      6. glycerol dehydrogenase
      26. glyoxylate reductase
      27. L-lactate dehydrogenase
      37. malate dehydrogenase
      49. glucose 6-phosphate dehydrogenase
      17. mannitol 1-phosphate dehydrogenase
    1.1.2 With cytochrome as an acceptor
      3. L-lactate dehydrogenase
    1.1.3 With O$_2$ as acceptor
      4. glucose oxidase
      9. galactose oxidase
  1.2 Acting on the CH-NH$_2$ group of donors
  1.4.3 With O$_2$ as acceptor
    2. L-amino acid oxidase
    3. D-amino acid oxidase
  1.6 Acting on reduced NAD or NADP as donor
  1.6.99 With other acceptors diaphorase
  1.10 Acting on diphenols and related substances as donors
    1.10.3 With O$_2$ as acceptor
      1. polyphenol oxidase
      3. ascorbate oxidase
  1.11 Acting on H$_2$O$_2$ as acceptor
    1.11.1
      6. catalase
      7. peroxidase
3. Hydrolases
  3.1 Acting on ester bonds
    3.1.1 Carboxylic ester hydrolases
      7. cholinesterase
    3.1.3 Phosphoric monoester hydrolases
      1. alkaline phosphatase
    3.1.4 Phosphoric diester hydrolases
      3. phospholipase C
  3.2 Acting on glycosyl compounds
    3.2.1 Glycoside hydrolases
      1. α-amylase
      4. cellulase
      17. lysozyme
      23. β-galactosidase
      27. amyloglucosidase
      31. β-glucuronidase
  3.4 Acting on peptide bonds
    3.4.2 Peptidyl-amino acid hydrolase
      1. carboxypeptidase A
    3.4.4 Peptidyl-peptide hydrolase
      5. α-chymotrypsin
      10. papain
  3.5 Acting on C-N bonds other than peptide bonds
    3.5.1 In linear amides
      5. urease
  3.6 Acting on acid anhydride bonds
    3.6.1 In phosphoryl-containing anhydrides
      1. inorganic pyrophosphatase
4. Lyases
  4.1 Carbon-carbon lyases
    4.1.2 Aldehyde lyases
      7. aldolase
  4.2 Carbon-oxygen lyases
    4.2.1 Hydrolases
      1. carbonic anhydrase
  4.3 Carbon-nitrogen lyases
    4.3.1 Ammonia lyases
      3. histidase Of particular interest are the dehydrogenases, illustrated by malate dehydrogenase and glucose-6-phosphate dehydrogenase, the hydrolases, such as β-galactosidase and lysozyme, and peroxidases.

In the next group of compounds are the mercaptan compounds, which may have a mercaptan group naturally or may have a mercaptan group introduced. With a naturally occurring compound of interest having a plurality of mercaptan groups, it will frequently be necessary to deactivate such groups by functionalizing them with permanent or removable groups. Usually, the functionalization will be by the formation of a thioether. Therefore, when the compound of interest has a plurality of mercaptan groups present, the compound of interest will be treated with a reagent which will react with the mercapto groups to prevent their subsequent reaction in the conjugation and a mercaptan group then introduced synthetically to provide the unique site of conjugation.

Similar considerations are involved with the polyamino functionalized compound. Where the polyamino functionalized compound has one or more active mercapto groups, these may be deactivated prior to introduction of the α-haloalkyl carbonyl compound.

The compounds of interest will generally have either hydroxyl or amino functionalities or both as sites for conjugation to a disulfide linkage. The linking functionality will normally be an ester, amide or ether. Where a plurality of functionalities are present in the molecule of interest, which functionalities may react with the disulfide compound, it will frequently be necessary to protect the other functionalities with removable groups prior to conjugation of the disulfide containing compound. In some instances, a mercapto group will be naturally present, and this can serve as the site for linking without synthetic introduction of a mercaptan.

For the most part, the mercapto compounds and their precursors will have the following formula:

EM(Q)$_a$TSU wherein:

E—the compound of interest, which will be discussed in more detail subsequently, which may be modified by introduction of an hydroxyl or amino functionality, by protection of one or more reactive functionalities with protective groups, desirably removable, or in any other manner appropriate to the purpose of its intended use;

M—O, NH

Q—C=W, wherein W is O, NH or S, particulary O,

T—a linking group having at least one carbon atom and not more than 9 atoms, other than hydrogen, usually one to four atoms, which are carbon, oxygen, nitrogen and sulfur, preferably carbon, the terminal atoms being carbon atoms, any oxygen is present as oxy ether or oxo, particularly non-oxo carbonyl; nitrogen is present as amido or bonded solely to carbon and hydrogen e.g. amino, primary, secondary or tertiary; and sulfur is present as thiono or thioether; the number of heteroatoms being in the range of zero to 4, usually zero to 2; T is preferably hydrocarbon, more preferably alkylene, there being not more than one site of aliphatic unsaturation, either branched or straight chained, preferably straight chained, particularly methylene or polymethylene $(CH_2)_b$, where b is from 1 to 4;

S—sulfur

U—H, alkylthio of from one to four carbon atoms, particularly methyl, or an alkali metal cation of atomic number 3 to 19;

a—zero or 1.

Where E has a natural occurring mercaptan group, M and T are taken together to form a single bond, a is zero and U is hydrogen.

Depending upon the purpose of the conjugate, the mercaptan containing compound may vary widely. Of particular interest are conjugates to enzymes which are intended for use in immunoassays. Of greater interest, are those enzyme conjugates which are employed in a homogeneous enzyme immunoassays as described in U.S. Pat. No. 3,817,837. In these conjugates, when antibody binds to the mercapto compound conjugated to the enzyme, there is a substantial reduction in the enzymatic activity. Therefore, it is quite advantageous once one has developed a particular distribution of active sites for a particular enzyme, that the mercapto compounds will bond substantially to the same sites, regardless of the nature of the mercapto compound.

Another use for the conjugates is for forming antigenic products for haptens, so as to be able to produce antibodies. In this situation, any non-antigenic compound may be bonded to a convenient polypeptide or protein, desirably a relatively large number of haptenic compounds being conjugated to the polypeptide or protein.

A third possibility is the conjugation of a label to a polypeptide or protein for use in an immunoassay for determination of the polypeptide or protein. Labels can take many forms. One class of labels is fluorescent compounds. Another class of labels is labels having enzymatically labile bonds. In this instance, the labile bond may be bonded distant from the thio ether linkage or may be part of the linkage between the compound of interest and the polypeptide or protein. Thus, the link between the compound of interest and the polypeptide or protein may be cleaved by an enzyme. These types of compounds include coenzymes, fluorescent compounds, chemiluminescent compounds, chemical catalysts, electron transfer agents, dyes, and the like.

The first group of compounds are monoepitopic ligands, which are generally involved in assays for their determination. These include drugs which are used for therapeutic purposes, naturally occurring physiological compounds, metabolites, pesticides, pollutants, and the like.

Included among drugs of interest are the alkaloids. Among the alkaloids are morphine alkaloids, which includes morphine, codeine, heroin, dextromethorphan, their derivatives and metabolites; cocaine alkaloids, which includes cocaine and benzoyl ecgonine, their derivatives are metabolites; ergot alkaloids, which includes the diethylamide of lysergic acid; steroid alkaloids; iminazoyl alkaloids; quinazoline alkaloids; isoquinoline alkaloids; quinoline alkaloids; which includes quinine and quinidine; diterpene alkaloids, their derivatives and metabolites.

The next group of drugs includes steroids, which includes the estrogens, gestrogens, androgens, andrenocortical steroids, bile acids, cardiotonic glycosides and aglycones, which includes digoxin and digoxigenin, saponins and sapogenins, their derivatives and metabolites. Also included are the steroid mimetic substances, such as diethyl stilbestrol.

The next group of drugs is lactams having from 5 to 6 annular members, which include the barbiturates, e.g. phenobarbital and secobarbital, diphenylhydantoin, and their metabolites.

The next group of drugs is aminoalkylbenzenes, with alkyl of from 2 to 3 carbon atoms, which includes the amphetamines, catecholamines, which includes ephedrine, L-dopa, methyldopa, epinephrine, narceine, papaverine, their metabolites and derivatives.

The next group of drugs if benzheterocyclics which include benzothiadiazides, oxazepam, chlorpromazine, tegretol, imipramine, their derivatives and metabolites, the heterocyclic rings being azepines, diazepines, thiadiazines, and phenothiazines.

The next group of drugs is purines, which includes theophylline, caffeine, theobromine, their metabolites and derivatives.

The next group of drugs includes those derived from marijuana, which includes cannabinol and tetrahydrocannabinol.

The next group of drugs includes the vitamins such as A, B, C, D, E and K.

The next group of drugs is prostaglandins, which differ by the degree and sites of hydroxylation and unsaturation.

The next group of drugs is antibiotics, which includes macrolides, aminoglycosides, β-lactams, etc. such as penicillins, ethambutol, isoniazid, vancomycin, methenamine madelate, chloromycetin, actinomycetin, tetracyclines, terramycin, cephalosporins, erythromycin, rifampin, clindamycin the aminoglycosides such as streptomycin, gentamicin, tobramycin, amikacin, kanamycin, neomycin; nalidixic acid, nitrofurantoin, colistimethate, lincomycin, amphotericin B, flucytosine, their metabolites and derivatives.

The next group of drugs is the nucleosides and nucleotides, which include ATP, NAD, FMN, adenosine, guanosine, thymidine, uridine and cytidine with their appropriate sugar and phosphate substituents.

The next group of drugs is miscellaneous individual drugs which include methadone, phenoxybenzamine and related haloalkylamines, tolamol, sotalol, guanethide, meprobamate, serotonin, merperidine, chlorcyclazine, chlorpheniramine, amitriptyline, nortriptyline, lidocaine, procaineamide, acetylprocaineamide, propanolol, griseofulvin, butyrophenones, antihistamines, methotrexate, aminopterin, anticholinergic drugs, such as atropine, their metabolites and derivatives.

The next group of compounds is amino acids and small peptides which include polyiodothyronines e.g. thyroxine, and triiodothyronine, oxytocin, ACTH, angiotensin, endorphin, met- and leu-enkephalin, their metabolites and derivatives.

Metabolites related to diseased states include spermine, galactose, phenylpyruvic acid, and porphyrin type 1.

Among pesticides of interest are polyhalogenated biphenyls, phosphate esters, thiophosphates, carbamates, polyhalogenated sulfenamides, their metabolites and derivatives.

Electron transfer labels will for the most part be either metal complexes or aromatic compounds.

Compounds of interest are ligands, particularly haptenic ligands, bonded to poly(amino acids), particularly antigen and enzymes. These compounds will have for the most part the following formula:

$$\left( EM(Q)_a TSCH_2 \overset{Y}{\overset{\|}{C}} ((A)_k (D)_m \overset{Y^1}{\overset{\|}{(C)}}_m)_m \right)_j - PAA$$

wherein all of the symbols have been defined previously except:

PAA—poly(amino acid); and j—a number on the average of at least one and not more than the molecular weight of PAA divided by 1,500, usually 2,000, generally in the range of 1 to 20. When PAA is an enzyme, j will generally be 1 to 20, usually 1 to 12 and more usually 2 to 12.

Of particular interest are compounds where PAA is an enzyme and E is a hapten of about 125 to 2,000 molecular weight. These compounds of interest for the most part will have the following formula:

$$\left( E^1 M(Q)_a T^1 SCH_2 \overset{Y^2}{\overset{\|}{C}} ((NH)_k (D^1)_m \overset{Y^2}{\overset{\|}{(C)}}_m)_m \right)_j - ENZ$$

wherein:

ENZ—an enzyme bonded through amino groups to form amide or amidine bonds;

$E^1$—an haptenic ligand of from about 125 to 2,000 molecular weight, usually from about 125 to 800 molecular weight;

$T^1$—a linking group of from 1 to 6, usually 1 to 4 carbon atoms, usually aliphatic hydrocarbon having from 0 to 1 site of ethylenic unsaturation and preferably saturated, either branched or straight chain, perferably straight e.g. $(CH_2)_q$, where q is a number of from 1 to 4;

$Y^2$—the two $Y^2$s are the same or different and are O or NH, preferably O;

$D^1$—is a linking chain of from 1 to 9, usually 1 to 5 and more usually 1 to 3 carbon atoms, preferably aliphatic hydrocarbon having from 0 to 1 site of ethylenic unsaturation, preferably saturated, either straight chain or branched, preferably straight chain e.g. $(CH_2)_q$, where q is a number of from 1 to 4;

$j^1$—is on the average a number of at least one and not more than 20, usually from about 1 to 12, more usually from about 1 to 8.

Enzymes of particular interest are oxidoreductases e.g. dehydrogenases, and hydrolases.

A narrower genus involves the conjugation of aminoglycoside antibiotics with enzymes, particularly oxidoreductases and hydrolases, many of which have been referred to earlier. These compounds will for the most part have the following formula (excluding chirality):

$$\left( \begin{array}{c} R^{11} \overset{R^1}{\diagdown} \quad R^5 \quad R^4 \quad \overset{R^{10}}{\diagdown} R^6 \\ \diagdown O \diagdown \quad \diagdown O \diagdown \quad -R^7 \\ R^{12} \quad R^2 \quad R^3 \quad R^9 \quad R^8 \end{array} \right)_z ENZ$$

wherein:

$R^2$ is amino (-NH$_2$), except for kanamycin A and amikacin where it is hydroxyl;

$R^3$ is hydroxyl;

$R^4$ and $R^5$ are amino except for amikacin, where $R^4$ is 2-hydroxy-4-aminobutyramido;

$R^6$ is hydrogen or methyl, being methyl when gentamicin and hydrogen when tobramycin, kanamycin or amikacin;

$R^7$ and $R^9$ are hydroxyl;

$R^8$ is amino or methylamino, being methylamino when gentamicin and amino when tobramycin, kanamycin or amikacin;

$R^{10}$ is hydrogen or hydroxymethyl being hydrogen for gentamicin and hydroxymethyl for tobramycin, kanamycin and amikacin;

$R^{11}$ and $R^{12}$ are hydrogen or hydroxy, being hydrogen for gentamicin, and hydroxyl for kanamycin and amikacin and $R^{11}$ is hydroxyl and $R^{12}$ is hydrogen for tobramycin;

$R^1$ is hydroxymethyl for kanamycin C and is otherwise FCHNHF$^L$, wherein F and $F^1$ are hydrogen or methyl, being methyl for gentamicin $C_1$, F being methyl and $F^1$ being hydrogen for gentamicin $C_2$ and otherwise hydrogen;

with the proviso that any of the amino (includes methylamino) groups may be substituted with an inert, normally removable, acylating agent of from 1 to 6, usually 1 to 2 carbon atoms e.g. trifluoracetyl, and one of the R groups which is amino has a linking group replacing a hydrogen to form a covalent bond to the enzyme ENZ; and z is on the average at least one and not greater than about 20, usually not greater than about 16 and preferably not greater than about 12.

The linking group has been described previously. Preferably, $R^1$, $R^4$ or $R^5$ serve as the linking site.

Polyepitopic ligands have been listed previously for the polyamino functionalized compounds. In addition, polysaccharides could be used to form the mercapto derivative. Where there is a plurality of functionalities on the compound to be derivatized as a mercapto compound, and it is desired that there be only one mercapto site, very light labeling can be employed and the unreacted material either recovered initially or after conjugation to the haloalkyl compound. In accordance with this method, where a polyfunctionalized compound is to be conjugated to a polyamino functionalized compound, the method affords a convenient way of linking with minimal or no polymerization.

Another group of compounds are the co-enzymes which include nicotinamide adenine dinucleotide, flavins, such as riboflavin and flavin adenine dinucleotide, pantothenic acids, cobalamines, ubiquinones, etc. Another group of compounds are fluorescent compounds which include the xanthene dyes e.g. fluoresceins derivatized from 3,6-dihydroxy-9-phenyl xanthhydrol, rosamines and rhodamines, derived from 3,6-diamino-9-phenylxanthhydrol; naphthylamines, such as 1-dimethylaminonaphthyl-5-sulfonate, 1-anilino-8-naphthalenesulfonate and 2-p-touidinyl-6-naphthalenesulfonate, 3-phenyl-7-isocyanatocoumarin; acridines, such as 9-isothiocyanatoacridine and acridine orange; N-p-2-benzoxazolyl(phenyl)maleimide; benzoxadiazoles, such as 4-chloro-7-nitrobenzo-2-oxa-1,3-diazole and 7-p-methoxybenzylamino(4-nitrobenzo-2-oxa-1-3, diazole); stilbenes, such as 4-dimethylamino-4'-isothiocyanatostilbene; N,N'-dioctadecyloxycarbocyanine p-toluenesulfonate; pyrenes, such as 8-hydroxy-1,3,6-pyrenetrisulfonic acid and 1-pyrenebutyric acid; merocyanine; rose bengal; 2,4-diphenyl-3(2H)-furanone, etc.

Chemiluminescent compounds include luminol and luciferin.

The above list while including a substantial number of compounds of interest, is not intended to be exhaustive, there being other additional compounds which may also be conjugated in accordance with the subject method.

CONJUGATION

The first reaction is the reaction with the polyamino functionalized compounds and the haloacyl compound. Normally, aqueous solvents will be employed, which may have up to 40 volume percent of inert polar solvents, such as alkanols, of from 1 to 4 carbon atoms, ethers, of from 2 to 6 carbon atoms, dimethylformamide, oxyalkylene alcohols and ethers of from 2 to 8 carbon atoms with alkylene groups of from 2 to 3 carbon atoms, dimethylformamide, hexamethylphosphoramide, and the like. The pH of the system will be at least about 6.5, usually at least 6.7 and generally not exceeding 9, more usually not exceeding about 8.5. Various conventional buffers may be used, such as phosphate. Tris, borate, etc. with one or more buffers being preferred in a particular system. The temperature for the reaction will generally be not less than about −5° C. and usually not greater than about 40° C., more usually from about −5° to 25° C. The choice of temperature is primarily a factor of denaturation and concern with enhancement of the activity of the halogen, where significant reaction with amino groups may occur.

The concentration of the polyamino compound may be varied widely, usually being not less than about 1 μg/ml and generally being not more than about 5 g/ml, conveniently being in the range of about 0.1 to 2 g/ml. The particular concentration is not critical to this invention and is primarily one of convenience, depending upon the molecular weights of the compounds involved, their solubility in the solvent, and the like. The amount of haloacyl compound added will vary widely depending on the degree of conjugation desired, the reactivity of the haloacyl compound, the rate of reaction desired and the like. Usually, not more than about a 10-fold excess will be employed, preferably not more than about a 5-fold excess.

The time for the reaction will vary widely depending upon the compounds involved, the temperature employed, the relative concentrations, the degree of conjugation desired, and the like. The reaction may be carried out over a few minutes or over many weeks.

After conjugation, the product may be worked up in accordance with conventional ways, such as dialysis, chromatography, precipitation, solvent extraction, and the like.

Depending upon the particular compounds involved, other ancillary materials may also be included in the reaction mixture.

Some variation in the technique will be involved depending upon the particular functionality which is employed for the conjugation. For the most part, the conditions will be comparable regardless of the active functionality which reacts with the amines.

The conjugation of the mercapto introducing compound with the compound of interest can employ a wide variety of the compounds with differing thio functionalities e.g. thioether with a displacable group, thiolactones and disulfides. Conveniently, the various thio groups may be conjugated employing an activated non-oxo carbonyl group in accordance with conventional procedures, normally forming esters and amides.

The conjugation for introduction of the mercaptan through the dithio-non-oxo carbonyl compound may be carried out in a wide variety of solvents, depending upon whether one is concerned with denaturation or not. Any solvent for the reactants which is inert may be employed, either aqueous or non-aqueous. Illustrative solvents include water, alkanols of from 1 to 6 carbon atoms, ethers of from 2 to 6 carbon atoms, dimethylformamide, dimethylsulfoxide, hexamethylphosphoramide, mixtures thereof, and the like. Reaction temperatures will normally be in the range of about −10° to 50° C., more usually in the range of about −5° to 25° C. The compounds will be combined at moderate concentrations, generally ranging from about 0.1 to 1 g/ml. The ratio of the disulfide to the compound of interest will usually be stoichimetric and up to about 50% in equivalent excess, more usually up to about 25% in equivalent excess. The reaction time may take a few minutes to a few days after which time the product may be isolated in accordance with conventional procedures which have been described previously.

The non-oxo carbonyl group may be activated in a number of ways. Conveniently, carbodiimide may be used with the acid directly. Preferably, an active ester will be prepared first and the ester conjugated. As appropriate, mixed anhydrides, isocyanates, isothiocyanates, and imidates may find use.

The disulfide group may be readily cleaved by conventional reactions, for example by combining the disulfide with dithioerythritol in an inert polar solvent at moderate temperatures in the absence of air and removing any mercaptan which forms by a rapid stream of an inert gas through the reaction solution. Concentrations may vary widely, and moderate temperatures will be employed in the range of about −10° to 50° C., more usually about −10° to 25° C. The reductant may be used in stoichiometric amounts or in mild excess, usually not exceeding 5-fold excess.

The thioether may employ various displaceable groups as one of the substituents on the sulfur. Conveniently, the displaceable group will be a carbocylic aromatic having from 1–3 electron withdrawing functionalities bonded in the ortho and para positions, particularly nitro, cyano, halo, sulfonyl, etc., where the aryl group may be displaced by mercaptide to leave a mercapto group bonded to the compound of interest.

The thioether may be conjugated to the compound of interest through the non-oxo carbonyl functionality in conventional ways, as described previously for the dithio compound.

The thioether is conveniently cleaved employing a mercaptide under mild basic conditions in an inert polar solvent, using at least stoichiometric amounts of the mercaptide e.g. mercaptoethanol, at a temperature of about −10° to 30° C.

The thiolactone will generally have a ring of from 4–6, more usually 5–6 members and may or may not be substituted. The reaction is carried out in a polar solvent e.g. water, using approximately stoichiometric amounts. The resulting mercaptide may be used directly without further purification.

The mercapto compound and the haloacyl compound will then be combined, normally in aqueous solvents as described previously. The pH of the solution will generally be at least about 6.5 and not greater than 8.5, more usually in the range of about 7 to 8. Stoichiometric amounts of the haptan may be added or mild excesses, usually not exceeding about 5-fold excess, more usually not exceeding about 2-fold excess. The buffers employed may be those described previously. Temperatures will generally range from about −10° to 40° C. usually about −5° to 25° C. The concentration of the reactants may be varied widely, generally ranging from about 0.01 to 100 mg/ml, depending upon the nature of the reactants. The reaction time may vary widely, being at least about 0.5 hrs. and may extend for weeks. At the end of the reaction, the product may be isolated in accordance with conventional procedures, these procedures having been indicated previously.

As illustrative of the subject method, its application to the conjugation of an aminoglycoside e.g. gentamicin to an enzyme e.g. glucose-6-phosphate dehydrogenase, will be described.

Gentamicin $C_1$ was trifluoroacetylated with thioester to deactivate the $C^{2'}$-amino under mild conditions (0°–40° C.) in an anhydrous alkanolic solvent of from one to four carbon atoms, particular methanol with a lower alkyl (one to four carbon atoms) trifluoroacetate in an approximately stoichiometric ratio.

After isolating the product, it was combined with an active amine acylating form of methyldithioacetic acid. Conveniently, an active ester may be employed, with the hydroxyl derived from compounds such as substituted phenols e.g. p-nitrophenol, N-hydroxy succinimide, etc. An inert polar organic solvent is employed, conveniently a polar ether of from 3 to 8 carbon atoms and the reaction carried out under mild conditions e.g. 10°–40° C., for a sufficient time to go substantially to completion. The product is isolated and reduced in an inert environment with conventional reductants e.g. dithioerythritol, mercaptoethanol, etc., with the methyl mercaptan swept from the solution with a rapid inert gas stream.

Meanwhile, the polyamino functional compound may be functionalized with active halogen. In this illustration, an enzyme is functionalized, particularly glucose-6-phosphate dehydrogenase. A bromoacetyl group is desirably introduced, which may be conjugated directly or conjugated as an N-substituent or an aminoacid of from about two to six carbon atoms. The carboxylic acid is activated, preferably as an active ester. Active alcohol moieties have been described previously. The enzyme is dissolved in an aqueous solution, buffered to a pH of about 7 to 9.5, preferably about 8 to 8.5, and the bromoacetyl compound added slowly, monitoring the change in enzyme activity, terminating the reaction when the desired ratio of bromoacetyl compound to enzyme is added or has been diminished to a predetermined level. The concentration of enzyme will generally range from about 0.05 to 5 mg/ml, but the concentration is not critical and is primarily a matter of convenience.

The conjugated enzyme may be isolated and purified, for example, by dialysis at a neutral or mildly acidic pH e.g. 5–7.

To the conjugated enzyme at a mildly basic pH between 7 and 8, in an aqueous medium at a moderate temperature, generally between −5° to 20° C., preferably about 0° to 10° C., is added the mercapto compound over a period of time. That is, aliquots are added rather than the mercapto compound being added all at once. The particular rate of addition will vary widely and, therefore, cannot be specifically set forth. The time for the reaction may vary from about 0.5 hour to one or more weeks.

At the end of the reaction the product may be purified in accordance with known techniques e.g. dialysis at moderately basic pH, 7.5 to 9.

The following examples are offered by way of illustration, and not by way of limitation.

EXPERIMENTAL (All temperatures not otherwise indicated are in centigrade. All percents not otherwise indicated are by weight. Parts are by weight except when two liquids are involved and are then by volume. Abbreviations are as follows: DMF-dimethylformamide; THF-tetrahydrofuran; NHS-N-hydroxy succinimide; G-6-PDH-glucose-6-phosphate dehydrogenase; NADH-nicotinamide adenine nucleotide (reduced); G-6-P-glucose-6-phosphate

EXAMPLE 1

Preparation of morphine and G-6-PDH conjugate

A DMF solution of bromoacetic acid (1 M, $^{14}$C,66 microcuries/millimole) was chilled to −10° under nitrogen and 127 mg N-hydroxy succinimide and 211 mg of 1-ethyl-3-dimethylaminopropylcarbodiimide hydrochloride (ECDI) were added with stirring. After stirring for a short while the temperature was raised to 0° and the mixture stirred for an additional 5 hrs., followed by storage at 4° for about 30 hrs.

An aqueous solution of 75 mg glycine dissolved in 2 ml water was added slowly with stirring to the above solution at 0°, the addition requiring 10 min. The final pH of 2.9 was raised to 5.4 by the slow addition of 10 N aqueous sodium hydroxide which was added with vigorous stirring over 5 min. at 0°. Over the next 25 min, 0.095 ml of 10 N sodium hydroxide was slowly added with stirring to maintain the pH at about 7. After 7 days at 4°, the pH had drifted to 6.7. The reaction was terminated by addition of 5 drops 48% HBr at 0° with stirring to lower the pH to 4.6 and 1 ml of 2 N sodium diacid phosphate added to give a final pH of 4.2. The aqueous solution was extracted with ethyl acetate, followed by lowering the pH to 3.05 by the addition of 8.5 drops of 48% HBr with stirring at 0°. The ethyl acetate extraction was repeated and the two ethyl acetate fractions and aqueous layer analyzed for radioactivity. The major share of the radioactivity was in the second organic fraction. Each of the ethyl acetate fractions had a total of about 12 ml.

The second fraction was evaporated to dryness to yield an oily solid weighing 57 mg. The product was a mixture of starting materials and product. Some removal of the bromoacetic acid was achieved by dissolving the mixture in chloroform, extracting with 3-4 ml portions of water and then extracting the aqueous portions with 3-4 ml portions of ethyl acetate. This was only partly successful, so the residue was triturated with 4-6 drop portions of dry benzene, until 8.4 mg of a product having the bromoacetamide of glycine and the NHS reactant in about a molar ratio of 2.5 to 1 was obtained. Since NHS was to be used to prepare the ester of the bromoacetamide of glycine, no further purification was carried out.

The entire product was dissolved in 200 μl of anhydrous DMF and 150 μl of anhydrous diglyme and the mixture stirred overnight under argon. To an aliquot of 89 μl was added 50 μl of anhydrous DMF containing 10 μM NHS and 10 μM ECDI and the solution allowed to stand overnight at 4°.

For conjugation to the enzyme, an enzyme solution was prepared by combining 160 μl of 0.05 M phosphate pH 8.0, 500 μl of water, 10 mg sodium G6P, 20 mg disodium NADH, 50 μl 1 M NaOH to adjust the pH to 8, 200 μl of a 1.04 mg/ml solution of G6PDH in 0.01 M phosphate followed by the further addition of 93 μl of water to provide a total volume of 1.03 ml. The mixture was cooled to 0° and the addition of the above NHS ester solution added slowly with vigorous stirring in aliquot portions of about 3 to 17 μl, alternating with the addition of approximately 1 N sodium hydroxide to maintain the pH in the range of about 8.2 to 8.3. The total amount of the NHS ester added was 78 μl. Forty minutes after the final addition, the enzyme was assayed and was found to have lost 82% of its activity.

The enzyme solution was quantitatively transferred to a dialysis sack using buffer washes (2×0.1 ml each) and dialyzed for seven days against 6×125 ml portions of pH 6.8, 0.01 M phosphate. The residue in the sack was removed quantitatively using buffer washes and made up to 2 ml. The solution was centrifuged at 17,500 rpm for 25 min. without removal of the turbidity which was present.

The conjugation number was determined employing the radioactivity of the bromoacetamide of glycine to indicate about 12 bromoacetylglycine groups per G6PDH.

$O^3$-[N-(Mercaptoethyl)carbamoylmethyl] morphine Hydrogen Oxalate (CMM) isobutyl mixed carbonic anhydride in $Me_2NCHO$ (15 ml, 0.10 M) was added dropwise over 15 min to aminoethanethiol (39 mg, 0.5 mmol) and triethylamine (210 ml, 1.5 mmol) in 1.0 ml of anhydrous dimethylformamide under nitrogen. The mixture was allowed to warm to room temperature over 1½ hours, the solvent was removed in vacuo at 40°, and the residual syrup was taken up in 3 ml of water and treated with 20 ml of 0.10 M sodium carbonate. Extraction of the mixture with ethyl acetate, washing with water, and evaporation in vacuo yielded a glass. To this glass were added under nitrogen, 10 ml of acetonitrile and 140 ml (1.0 mmol) of triethylamine followed by 77 mg (0.5 mmol) of dithioerythritol in 1.5 ml of acetonitrile. After standing for 20 min at room temperature and overnight at 0° the solution was evaporated in vacuo and treated with 5.0 ml of oxygen-free water and 1.0 ml of 1.0 M oxygen-free aqueous oxalic acid. The resulting solution was washed with ethyl acetate and evaporated to dryness in vacuo. The residue was triturated with 5 ml of ethanol and, after standing overnight at 0°, washed with 3 ml of fresh ethanol to give 117 mg (46%) of the product. A solution of 2.1 mg of the above bioxalate salt of the morphinethio compound in 200 μl of nitrogen saturated deionized water was prepared and 3 μl of about 1 M sodium hydroxide added to raise the pH to 5. To 1 ml of the N-bromoacetyl glycine-G6PDH conjugate was added 3.2 μl of about 1 N sodium hydroxide at 0° with stirring to raise the pH from 6.75 to 8.5. The solution was deaerated by bubbling argon through at 0° (4.5 ruby ball) for 20 min, followed by the addition of 50 μl of the morphinethiol solution in 5–10 μl portions with stirring over about 3 min. The solution was stirred for 30 min at 0°, followed by stirring for 75 min at room temperature and then stored for 14 days at about 4° under argon. The solution was then dialyzed against 5×125 ml portions of 0.01 M phosphate, pH 6.75 over 7 days.

The product was assayed for enzymatic activity, the effect of excess antimorphine, and the effect of the combination of excess antimorphine and codeine on the enzymatic activity. The procedure for determining enzymatic activity may be found in U.S. Pat. No. 3,875,031, the relevant portions pertaining to the assay method being incorporated herein by reference. The measurements were made over a 2 min period, with readings after the first and third minutes after all the materials were combined. The readings are reported in change of optical density over the two minute period. A 20 μl aliquot was dissolved in 0.9 ml of 0.055 M Tris, pH 7.9, and a 10 μl aliquot of this solution assayed in 1 ml of assay solution. The following are the results:

Table 1

| Anti Morphine[1] μl | Codeine[2] μl | ΔOD |
|---|---|---|
|  |  | 0.102, 0.107, 0.104 |
| 1 |  | 0.048 |
| 2 |  | 0.047 |
| 1 | 1 | 0.113 |

[1]M conc. of binding sites - $5.2 \times 10^5$M
[2]preincubated with antimorphine; $5 \times 10^{-4}$M The above results show that the conjugate retains substantial enzymatic activity and is capable of inhibition by antibodies so as to be useful in a homogeneous enzyme immunoassay. By adding the antibody to a sample containing morphine or a morphine derivative i.e. codeine, when the mixture is added to the enzyme conjugate, there is no inhibition. Thus, the product can be used in a homogeneous enzyme immunoassay for the determination of an haptenic compound e.g. codeine.

EXAMPLE 2

Conjugation of morphinethiol to bromoacetylated G6PDH

To 40 μl at 0° of a 1 normal bromoacetic acid solution in DMF ($^{14}C$, 100 microcuries/millimole) was added 200 μl of a chilled DMF solution containing 44 μM of NHS and 40 μM of ECDI and the mixture allowed to stand 2 days at 4° under argon.

An enzyme conjugation solution was prepared by combining 0.462 ml of 0.05 M phosphate, pH 6.7, 10 mg monosodium G6P, 20 mg disodium NADH, 0.039 ml 1 N sodium hydroxide, 0.348 ml water and 0.122 ml of a G6PDH solution having 0.803 mg/ml of G6PDH in 0.01 M phosphate to provide a final volume of 1 ml.

To the stirred mixture was added slowly in primarily 5 μl increments the NHS ester prepared above with invervening additions of 1 N sodium hydroxide added slowly to maintain the pH in the range of about 8 to 8.2. The total amount of NHS ester added was 30 μl. The total addition took less than 1 hr.

The solution was quantitatively transferred to a dialysis bag using 2×0.1 ml 0.05 M phosphate, pH 6.7 washes, and dialyzed with 5×125 ml portions of 0.01 M phosphate, pH 6.7 over 7 days at 0°. The hapten number was determined by virtue of having employed a radioactive bromoacetic acid and was found to be about 19.2. bromoacetyl groups per G6PDH.

A solution of the morphinethiol bioxalate prepared as described above was prepared by dissolving 5.37 mg of the salt in 340 μl water and adding slowly with a syringe and stirring 9 μl of 1 N sodium hydroxide to provide a final pH of 6.0. Following the same procedure as described previously, the enzyme conjugation solution was cooled to 0°, 2 μl sodium hydroxide added to provide a pH of 8.3, the solution saturated with argon for 40 min (5.5 ruby ball) and 50 μl of the morphinethiol solution added slowly. The mixture was then stored under argon at 4° for 30 days. At the end of this time, the mixture was transferred to a dialysis sack and dialyzed against 5×125 ml portions of 0.01 M phosphate, pH 7.0 for several weeks at 0°.

A 10 μl aliquot was assayed as described above, except that a 7 min period was employed from the 1st to 8th minute after mixing and the ΔOD was 0.078, 0.077. Upon addition of 4 μl of antibody, the ΔOD dropped to 0.043, 0.042.

The above results demonstrate that an active enzyme can be obtained by conjugation in accordance with the subject method, which is inhibitable by the binding of antibody to the specific hapten. Therefore, the product permits the use of the enzyme in a homogeneous enzyme immunoassay.

EXAMPLE 3

Conjugation of gentamicin to G6PDH

A. Strongly basic, quaternary ammonium (polystyrene) type (aminated with trimethylamine) anion exchange resin-$RN(CH_3)_3^+Cl^-$-was transformed to $RN(CH_3)_3^+OH^-$ form with 1 N NaOH. A column of 45 cm×3 cm required 8 l. of 1 N NaOH and was rinsed to neutrality with 4 l. of deionized water. A 5 g sample of gentamicin sulfate was eluted with 850 ml of water to give 3 g of free base after lyophilization. After being dryed over $P_2O_5$ under reduced pressure it weighed 2.7 g, mp. 90°–120°.

B. Gentamicin sulfate (10 g) was suspended in 100 ml of anhydrous methanol. Ammonia gas was introduced with stirring. The suspension became thinner and the mixture began to warm up. The mixture was cooled by ice bath and saturated with $NH_3$ for one hour. After filtration the solid cake was treated once more as above. The combined filtrate was concentrated to give 6.5 g of free base with a trace amount of sulfate as indicated by tlc.

C. Liquid partition chromatography was used in this separation. A column of 5 cm×85 cm was packed with 500 g (60–200 mesh) of silica gel. The eluent is the lower phase of the following solvent mixture: $CHCl_3$/isopropyl alcohol/17% $NH_4OH$ in a ratio of 2/1/1.

Five grams of gentamicin complex was dissolved in a mixture of methanol and chloroform. To this solution was added silica gel (5 g) and the mixture concentrated to a dry powder. The mixture was placed on the top of the column, wetted with solvent, topped with 2–3 cm of sand and covered with a piece of filter paper. The column was eluted at ca. 2 ml/min. in the day time and 1 ml/min. at night. Gentamicin $C_1$ collected pure at 5 l. to 5.65 l. weighed 610 mg. It followed a long fraction of a mixture of $C_1$ and $C_2$. Then 900 mg of gentamicin $C_2$ was collected. The pure $C_{1a}$ isomer isolated was very small in quantity. Recovered gentamicin complex was 3.6 g.

D. Gentamicin $C_1$ (1 mmol, 477 mg) was dissolved in 5 ml of anhydrous methanol under argon and at room temperature. To this solution was added ethyl trifluoroacetate (1 mmol, 160 mg) and the mixture was stirred overnight. Analytical tlc (silica, $CHCl_3$/MeOH/conc. $NH_4OH$:10/10/3) showed approximately 60% reaction but further reaction did not improve the yield. Pure product was isolated with a dry column of silica gel (60–200 mesh, 1 cm×23 cm; $CHCl_3$/MeOH/3 N $NH_4OH$:2/1/1). It had a $R_f$=0.64 on analytical tlc plate. Product isolated weighed 185 mg, yield 34.5%.

E. To 5 ml of anhydrous ethanol at 0° under argon was added ethyl chlorosulfenyl carbonate (3 g, 21.4 mmol). Methanethiol (2 ml, 36 mmol) was placed in a dropping funnel with a dry ice jacket and was added over an hour. The resulting mixture was stirred at room temperature for an additional hour. Concentration on a warm water bath and oil pump gave 1.6 g of product.

Ethyl methyldithiocarbonate (1.52 g, 10 mmol) prepared above was dissolved in 5 ml of deoxygenated methanol and mercaptoacetic acid (0.92 g, 10 mmol in 5 ml of methanol) was added dropwise in five minutes. The reaction was vigorous with gasing after the addition of 1.5 ml of $Et_3N$. The reaction mixture was stirred at room temperature for two hours and then subjected to degasing under the water aspirator. To the resulting mixture was added 20 ml of water and the aqueous solution extracted with 50 ml of $CH_2Cl_2$. The aqueous layer was extracted with 50 ml of saturated $NaHCO_3$. Upon acidification with 5 N $H_2SO_4$ to pH 2 and extraction by a mixture of $CH_2Cl_2$–$CHCl_3$ (total 120 ml), the product solution was washed with saturated brine and dried ($MgSO_4$). Concentration of the solution gave a colored liquid which weighed 550 mg.

F. Methyl dithioacetic acid (0.22 mmol, 30 mg), NHS (0.22 mmol, 25 mg), dicyclohexyl carbodiimide (0.22 mmol, 46 mg) and 3 ml of dry DMF were mixed at 0° and stored at 4° under argon overnight. The resulting solution was concentrated under reduced pressure to dryness, 3 ml of THF added, and the solution passed through a small column of cellulose powder and dropped directly into a solution of 2'-N-trifluoroacetylgentamicin $C_1$ (0.19 mmol, 107 mg) in 8 ml of dry THF. The addition took 0.5 hour and the reaction mixture was allowed to proceed at room temperature overnight. The resulting mixture was concentrated and passed through a small silica gel column, first with 1:1 chloroform-hexane, then 10% MeOH in chloroform and finally with $CHCl_3$/methanol/3 N $NH_4OH$:2/1/1. The product was eluted with the final solvent system. The pure compound weighed 30 mg, $R_f$=0.76.

G. Bromoacetylglycine (0.2 mmol, 38 mg), NHS (0.2 mmol, 22 mg), and ECDI (0.2 mM, 38 mg) were dissolved in 1 ml of anhydrous DMF in an ice bath under argon. The capped mixture was stirred in a cold room overnight. The tan colored solution was stored in the freezer ready for use.

A one milliliter G6PDH solution was prepared by mixing in an ice bath: G-6-P monosodium salt (10 mg), NADH disodium salt trihydrate (20 mg), phosphate buffer (0.05 M, 152 µl) and G6PDH (in 0.01 M phosphate buffer, 1.76 mg/ml, 568 µl). The final concentration of enzyme was 1 mg/ml at pH 8.25. To this enzyme solution at 0° was added slowly the NHS ester of bromoacetylglycine solution prepared above in 2 µl portions, and the pH adjusted carefully as needed. The total NHS ester added over 95 min was 7 µmol (35 µl), at which time the enzyme activity was approximately 23% of the original value. To the resulting solution was added 1 ml of phosphate buffer (1 N, pH 6.1) and the solution dialyzed in 5×110 ml of 0.01 M phosphate buffer at pH 6.8 in the cold room. The clean enzyme solution showed 24.6% original activity in a 1 min. assay at 340 nm.

H. 3-N-Methyldithioacetyl-2'-N-trifluoroacetylgentamicin $C_1$ (4.85 mg, 7 µmol) and dithioerythritol (1.08 mg, 7 µmol) were dissolved in 0.5 ml of 50/50 aqueous THF which was previously saturated with argon in an ice bath. The reaction solution was again saturated with argon, capped and stirred in the cold room overnight. The $CH_3SH$ generated was evaporated by passing through the solution a rapid stream of argon for 2 hours.

A bromoacetylglycyl-G6PDH solution (0.5 ml phosphate solution, 0.17 mg, $1.6 \times 10^{-6}$ mmol) was kept in ice bath and adjusted to pH 8.5 slowly and carefully with a pH meter. The solution of the above sulfhydryl gentamicin was added to the enzyme solution in 2 µl portions over 2 hrs. The pH was kept close to 7.5. After an additional hour of stirring the pH was 7.63. A total of 100 µl of the hapten was added (1.78 mg of hapten, 2.5 µmol). There was a deactivation from the original ΔOD 71 to ΔOD 33. This reaction solution was kept in the refrigerator for 4 days. The conjugate was then dialyzed with 8×100 ml of 0.2 M pH 8 phosphate over 4 days. The conjugate was very sticky and 1 mg/ml of aqueous rabbit serum albumin (RSA) in tris buffer (pH 7, M) was added to eliminate this problem.

EXAMPLE 4.

Conjugation of tobramycin with homocysteinthiolactone

To a solution of tobramycin (0.23 g, 0.5 mmol) in 5 ml of water at room temperature under nitrogen was added slowly a solution of 0.08 g (0.5 mmol) of homocysteinthiolactone in 2 ml of THF. The mixture was then stirred at room temperature under nitrogen for 2 hrs and could then be used directly for conjugation to a haloacetyl group as described in Example 3.

EXAMPLE 5.

Conjugation of thioglycolic ether with tobramycin

To a solution of thioglycolic acid (0.92 g, 10 mmol) and 1 ml of triethylamine in 10 ml of methylene dichloride at 0° was added 1.86 g (10 mmol) of 2,4-dinitrofluorobenzene. The mixture was then stirred at room temperature overnight and the volatiles removed in vacuo to leave a yellow residue. The residue was dissolved in ethyl acetate, and the solution washed with water and the organic layer then extracted with aqueous sodium bicarbonate. After washing the aqueous extract several times with ethyl acetate and acidifying with 2 N hydrochloric acid, the aqueous extract was extracted with ethyl acetate and the combined ethyl acetate extracts washed with water followed by brine, and then dried over anhydrous sodium sulfate. The solvent was removed in vacuo to leave a yellow solid which was recrystallized from ethyl acetate to yield 2 g (77.5%).

Into 10 ml of anhydrous DMF was dissolved 0.258 g (1 mmol) of 2,4-dinitrophenylthioglyclic acid and 0.115 g (1 mmol) of N-hydroxy succinimide. Under nitrogen at 0° was then added 0.287 g (1.5 mmol) of ECDI and the mixture stirred at 0° for 2 hrs followed by adding the mixture dropwise to a solution of 0.467 g (1 mmol) of tobramycin in a mixture of 12 ml water and 3 ml DMF. After stirring overnight at 0°, the solvent was removed in vacuo to yield a brownish residue which was triturated with methanol to yield a tan solid. The solid was filtered and dried in vacuo, followed by chromatography on silica prep plates eluting with a 1:2:1 solvent of chloroform: methanol: conc. ammonium hydroxide. Based on spectophotometric analysis, the product had an average of 1.4 thioether groups per tobramycin.

EXAMPLE 6.

Preparation of N-bromoacetyl glycine

To a solution of 4 g (0.02 mol) of t-butyl glycinate and 4 ml of pyridine in 100 ml of methylene dichloride at 0° under nitrogen was added a solution of 2.01 ml (0.024 mol) of bromoacetyl bromide in 10 ml of methylene dichloride. After the addition, the mixture was stirred for 3 hrs and poured into 1 N aqueous hydrochloride. The organic layer was separated and then washed successively with 1 N HCl, water and brine. After drying over anhydrous sodium sulfate, the mixture was evaporated to dryness in vacuo to yield 6 g of a light brown product, which upon recrystallization from hexane-ethyl acetate, yielded a product with mp 90°–91°.

The subject method finds particular use for conjugation of polyfunctionalized macrolides, such as the aminoglycosides. These compounds include streptomycin, gentamicin (1, 1a,2), tobramycin, kanamycin, amikacin, neomycin and paramycin.

The method may initially employ a protecting group, preferably removable, which may or may not be subsequently removed. Illustrative protective groups include trifluoroacetyl, carbobenzyloxy, etc. The remaining amino group or groups are then combined with a slight excess of an activated ester or mixed anhydride of an alkyldithioacetic under mild conditions, namely in the range of about −10 to 40° C., usually 0° to 25° C. in an inert polar solvent. Illustrative solvents include tetrahydrofuran, dimethylformamide, ethyleneoxy and propyleneoxy ethers, and the like. The reaction mixture may then be worked up in conventional ways, the disulfide cleaved to provide a thio compound, which may then be conjugated with a haloacetyl group as previously described.

The subject invention provides a simple technique for conjugating a variety of compounds to polyamino compounds, particularly where the compound to be conjugated to the polyamino compound is polyfunctional. In accordance with the subject technique, one can obtain a relatively constant distribution of active sites for conjugation to the polyamino compound. This method finds particular use where a variety of compounds are to be conjugated to the same polyamino compound, and substantially the same distribution of substitution is desirable. Illustrative of such a situation is the conjugation to enzymes, particulary where the enzymes are to be used in homogeneous enzyme immunoassays. Other applications are where the two compounds to be conjugated both have a plurality of amino groups, and one wishes to minimize the amount of polymerization of the product. Mild conditions can be used throughout, where heat labile materials are involved, such as frequently encountered with polypeptides and proteins.

Although the foregoing invention has been described in some detail by way of illustration and example for purposes of clarity of understanding, it will be obvious that certain changes and modifications may be practiced within the scope of the appended claims.

What is claimed is:

1. A method for covalently linking a poly(amino acid) compound being substantially free of active mercapto groups and having a plurality of amino functionalities to a mercapto compound, which comprises:

covalently linking at least one α-bromoacetyl containing compound to said poly(amino acid) through a non-oxocarbonyl group, including the nitrogen and sulfur analogs thereof, to form amide linkages or the nitrogen or sulfur analogs respectively, by combining said α-bromoacetyl containing compound with said poly(amino acid) in an inert polar solvent at a pH in the range of about 6.5 to 9 at a temperature in the range of about −5° to 40° C. to provide an α-bromoacetyl functionalized poly(amino acid); and combining said α-bromoacetyl functionalized poly(amino acid) compound with said mercapto compound under mild conditions in a polar medium at a pH of about 6.5 to 8.5 to form a thioether by displacement of said bromo with the sulfur of said mercapto.

2. A method according to claim 1, wherein said bromoacetyl functionality is introduced as N-bromoacetyl glycine.

3. A method according to claim 1, wherein said poly(amino acid) compound is an enzyme.

4. A method according to claim 4, wherein said bromoacetyl group is introduced as N-bromoacetyl glycine.

5. A method for covalently linking a poly(amino acid) having a plurality of amino functionalities and being substantially free of active mercapto groups to a mercapto compound which comprises:

combining a bromoacetyl functionality containing compound having a non-oxocarbonyl functionality with said poly(amino acid) to form through said non-oxocarbonyl functionality amide linkages, in an aqueous solvent at a pH of about 6.7 to 9 and at a temperature in the range of about −5° to 25° C. to provide a bromoacetyl functionalized poly(amino acid);

combining said bromoacetyl functionalized poly(amino acid) with a mercapto containing compound in an aqueous solvent at a pH of from about 7 to 8 at a mild temperature to form a thioether by displacement of said bromo with the sulfur of said mercapto.

6. A method according to claim 6, wherein said poly(amino acid) is an enzyme.

7. A method according to claim 7, wherein said enzyme is a dehydrogenase.

8. A method according to claim 8, wherein said mercapto compound is a hapten containing an hydroxyl or amino functionality having said mercapto group linked to said hydroxyl or amino functionality through a linking group.

9. A method according to claim 9, wherein said mercapto containing compound is an alkaloid.

10. A method according to claim 9, wherein said mercapto containing compound is an aminoglycoside.

11. A method for conjugating an aminoglycoside to a poly(amino acid) having a plurality of amino functionalities and being substantially free of active mercapto groups which comprises:

acylating said aminoglycoside with a sulfur functionality containing carboxylic acid compound:

modifying the sulfur functionality as required to provide a mercaptan to form a mercapto-substituted aminoglycoside;

acylating said poly(amino acid) with a bromoacetyl containing carboxylic acid compound to form a bromoacetyl substituted poly(amino acid) in an inert polar medium at a pH in the range of about 6.5 to 9 and at a temperature in the range of about −5° to 40° C.;

combining said mercapto-substituted aminoglycoside with said bromoacetyl substituted poly(amino acid) at a pH of from about 7 to 8 at a mild temperature, whereby said mercapto group displaces said bromo group to form a thioether to provide an aminoglycoside conjugated poly(amino acid).

12. A method according to claim 12, wherein said poly(amino acid) is an enzyme.

13. A method according to claim 13, wherein said enzyme is a dehydrogenase and said bromoacetyl compound is N-bromoacetyl glycine.

14. A method according to claim 14, wherein said aminoglycoside is a gentamicin.

* * * * *